United States Patent [19]

Falk

[11] Patent Number: 5,731,872
[45] Date of Patent: Mar. 24, 1998

[54] PLASMA MANIPULATOR

[75] Inventor: Heinz Falk, Kleve, Germany

[73] Assignee: Spectro Analytical Instruments GmbH, Kleve, Germany

[21] Appl. No.: 549,851

[22] PCT Filed: Feb. 8, 1995

[86] PCT No.: PCT/EP95/00447

§ 371 Date: Feb. 22, 1996

§ 102(e) Date: Feb. 22, 1996

[87] PCT Pub. No.: WO95/25951

PCT Pub. Date: Sep. 28, 1995

[30] Foreign Application Priority Data

Mar. 18, 1994 [DE] Germany ............... 44 09 237.7
Jun. 3, 1994 [DE] Germany ............... 44 19 423.4

[51] Int. Cl.⁶ ..................................... G01N 21/73
[52] U.S. Cl. ............................................ 356/316
[58] Field of Search ................................ 356/316

[56] References Cited

U.S. PATENT DOCUMENTS

| | | | |
|---|---|---|---|
| 4,395,091 | 7/1983 | Russo | 350/319 |
| 4,902,099 | 2/1990 | Okamoto et al. | 356/316 |
| 5,483,337 | 1/1996 | Barnard et al. | 356/316 |

FOREIGN PATENT DOCUMENTS 0 051 152 A1   5/1982   European Pat. Off.

OTHER PUBLICATIONS

P.W.J.M. Boumans, editor, "Inductively Coupled Plasma Emission Spectroscopy," John Wiley & Sons, New York, 1978.

D.R. Demers, "Evaluation of the Axially Viewed (End–on) Inductively Coupled Argon Plasma Source for Atomic Emission Spectroscopy," *Applied Spectroscopy*, vol. 33, No. 6, pp. 584–591 (1979).

*Primary Examiner*—F. L. Evans
*Attorney, Agent, or Firm*—Ware, Fressola, Van Der Sluys & Adolphson; Milton Oliver

[57]   ABSTRACT

The invention relates to a device for emission spectrum analysis with an analysis plasma containing the analysis sample and a spectrometer suitable for emission measurements, in which there is a plasma manipulator (4) with a cooled diaphragm (8) concentric with the axis (7) and perpendicular to the direction of expansion of the plasma with a free diameter smaller than that of the plasma which allows only the central part (6) or only the optical part of the analysis plasma to pass and masks off the remaining region, and an observation device (3) for the radiation emission of the volume of plasma allowed through.

12 Claims, 3 Drawing Sheets

PLASMA MANIPULATOR

The present invention relates generally to a device for shaping the observation zone of a plasma region for optical emission spectrum analysis.

It is desired that a device is to separate the region which guarantees low intensities of baseline radiation at the highest possible analytical emission signal from a non-conducting plasma containing the analysis sample. Furthermore, emission signals are to be stabilized against fluctuations and the ambient atmosphere is to be kept apart from the light path between the observation zone of the plasma and the spectrometer.

Various plasma radiation sources suitable for use in emission analysis are known. Using a carrier gas, analysis samples are commonly introduced as an aerosol into the plasma, where they are vaporized, dissociated, partly ionized, and the free atoms and ions are excited to a state of optical emission. Measurement of the emitted radiation usually takes place in an electrically non-conducting region of the plasma to keep influences of the sample matrix to a minimum. Examples of such sources of radiation include disc-stabilized arcs, inductively coupled plasma (ICP) and microwave induced plasma.

The analytical capability of the emission radiation sources described above increases with the signal-to-noise ratio (SNR), the quotient of the spectral line intensity of the verifiable species and the spectral baseline emission occurring in the spectrum interval in question. Through numerous experiments it has been established that SNR depends greatly on the type of optical observation. For example, observation of ICP along the vertical plasma axis shows that at a certain distance from the excitation coil, with said distance being dependent on the analysis element viewed, SNR is maximized (P. W. J. M. Boumans, Ed., Inductively Coupled Plasma Spectroscopy, John Wiley & Sons, New York, 1987). If ICP is observed in the direction of the plasma axis (end-on), the maximum SNR is reached in the center of the plasma and attention must be paid to the appropriate masking off of the hotter outer regions of the plasma having a radius of approximately 2 mm (D. R. Demers, "Evaluation of the axially viewed (end-on) Inductively Coupled Argon Plasma Source for Atomic Emission Spectroscopy", Applied Spectroscopy v. 33 (1979), p. 584).

Conventionally, the available methods of observation for electrically non-conducting plasmas mask off only a specific portion of the interfering baseline radiation. The spectrally continuous baseline radiation results mainly from interaction between plasma ions and electrons. In addition, the emission of molecules contributes to an increase in baseline radiation. The intensities of both kinds of baseline radiation increase with the rising temperature of the plasma at a greater rate than the desired light intensity. Optimal temperatures for various emission characteristics of atoms and ions used for the analysis vary considerably. When viewing the plasma either vertically or parallel to the axis, different temperature zones are registered. This factor limits the attainable SNR.

It is the object of the present invention to manipulate electrically non-conducting plasmas such that baseline radiation is reduced while the signal-to-noise ratio of the analytical measurement is increased.

This objective is accomplished by masking off that part of the region that is optimal for emission measuring by carrying out the observation in a volume area protected to a large extent from ambient influences and by making it possible to additionally optimize the composition of the plasma with electric or magnetic fields. The invention significantly improves the detection capability of the analysis procedure.

To this end, a cooled diaphragm is mounted concentric with the axis of the plasma in the flow direction. The diaphragm allows only the central part optimal for emission measurements and, in particular, only the optical part to pass through. In the direction of the flow behind the plasma there is a chamber which allows the plasma region selected to be observed along it vertically or in the direction of the axis. In order to guarantee optical transmission, the path between the plasma region and the measuring device is purged with an appropriate gas, preferably the carrier gas of the plasma. A plasma-manipulator comprises a cooled diaphragm, an observation chamber and a device connecting it to the spectrometer. By having an electric potential relative to the plasma potential applied to the inlet diaphragm, an optimization of SNR is attained due to the influence on the electron and ion concentration. Electrodes or magnetic pole shoes mounted inside the manipulator facilitate the creation of electric or magnetic fields either in front of or within the observation zone. Through a change in the charge carrier concentration in the plasma, these may also be used to optimize SNR. If an alternating voltage is applied to the manipulator and/or the electrodes in the manipulator, line intensity and baseline intensity are modulated in the rhythm of this alternating voltage. The phase-dependent evaluation of the subsequently modulated signals enables a distinction to be made between actual and noise signals, and with it the optimization of SNR.

To increase the speed of the plasma jet passing through the cooled diaphragm of the plasma manipulator, the creation of low pressure in the flow direction behind the observation zone can prove effective. The resulting increased flow velocity of the masked off plasma jet reduces temperature loss in the observation volume in the direction of expansion. It is advantageous to use a pump to create the reduced pressure conditions, with the discharge end of the pump being led back into the analysis plasma and in particular into the cooling gas flow so that the analysis plasma is better utilized.

The actual embodiment of the invention and the choice of operating parameters, such as plasma power, gas throughputs, distance between the plasma-producing device and the plasma manipulator as well as the selected electric potentials, depend on the one hand on the samples to be analyzed and on the other on the required detection limits. Additionally, the plasma axis can be configured either vertically or horizontally.

For a high signal-to-noise ratio it may prove advantageous in certain applications, for instance, to view the plasma with the observation device at an angle of 10 to 170 degrees (preferably between 45 and 135 degrees) against the expansion axis. In other cases it may be necessary to configure the observation device along the direction of expansion of the plasma and, therefore, to select the so-called end-on viewing position. At the same time the conical bore hole of the cooled diaphragm can be reproduced on an intermediate diaphragm.

A voltage can be applied between the plasma-producing device, especially an ICP burner tube, and the diaphragm of the plasma manipulator. In this manner either the plasma itself can be modulated electrically, or it can compensate for an electric potential which is generated between the plasma-producing device and the plasma manipulator.

Geometrically favorable conditions arise when the plasma manipulator has an inlet diaphragm of a thickness comparable to the diameter of the diaphragm and the observation volume has a diameter larger than that of the diaphragm.

If between the inlet diaphragm and the observation volume, particularly in the area of the observation volume, electrodes or pole shoes are mounted as a means of generating an electric and/or a magnetic field, in particular there being a coil in the area adjacent to the developed plasma jet, it is possible to shape the plasma in the observation volume either electrically or magnetically. An alternating voltage can be applied to the electrodes with the signal detection in the spectrometer being synchronized with the voltage, in this way improving the signal-to-noise ratio in a known manner. The modulation of the plasma is appropriately chosen such that the part of the signal that is significant for the viewed emission is altered with the modulation, while the baseline remains largely constant. Given the constant portion of the emission, a baseline correction of the signal received can be carried out.

At the outlet of the central plasma jet, the plasma manipulator can feature a diaphragm with a pipe socket for connecting a pump to facilitate the evacuation and reuse of plasma carrier gases or plasma manipulator purging gases. It is therefore advantageous for the ICP burner tube to be situated especially close to the plasma manipulator to minimize contact of the purging gas or carrier gas with the ambient atmosphere. Extreme embodiments of this design principle can feature the ICP burner tube (also torch tube) connected directly to the plasma manipulator; for instance, it can be welded or screwed on to the manipulator such that it is impossible for the plasma under observation and the purging gas to come into contact with the outside air. Evacuation is then favorably carried out via an annular gap in the plasma manipulator.

The plasma torch under observation can also be manipulated in such a way that an inert gas flow escapes from the plasma manipulator coaxial to the plasma torch and counter to its flow direction, thus reducing the actual light-emitting length of the plasma torch. In this manner, the plasma torch is dissipated in a funnel-like shape in the region where it meets the purging gas and the temperature gradient in this region increases significantly. As a result, when measuring elements such as Cadmium only a very specific, short region of the plasma torch has the temperature required for UV emissions and immediately following it (in the direction of the expansion of the plasma) there is a cold region which is substantially unable to emit any interfering UV light. By means of the flow of the gas supplied in counter direction, the length of the plasma torch being observed can be adjusted and the UV-emitting region appropriately selected specific to the element. A short plasma torch would be preferred for elements with high levels of excitation energy, while a long plasma torch is optimal for elements with low levels of excitation energy.

Further details and advantageous refinements of the invention are set forth in the following description and associated drawings of preferred embodiments, of which FIG. 1 is a first exemplary embodiment of the present invention;

Without exception these examples use ICP as the source of plasma, but they can be applied to other sources of excitation analogously.

Figure 1:
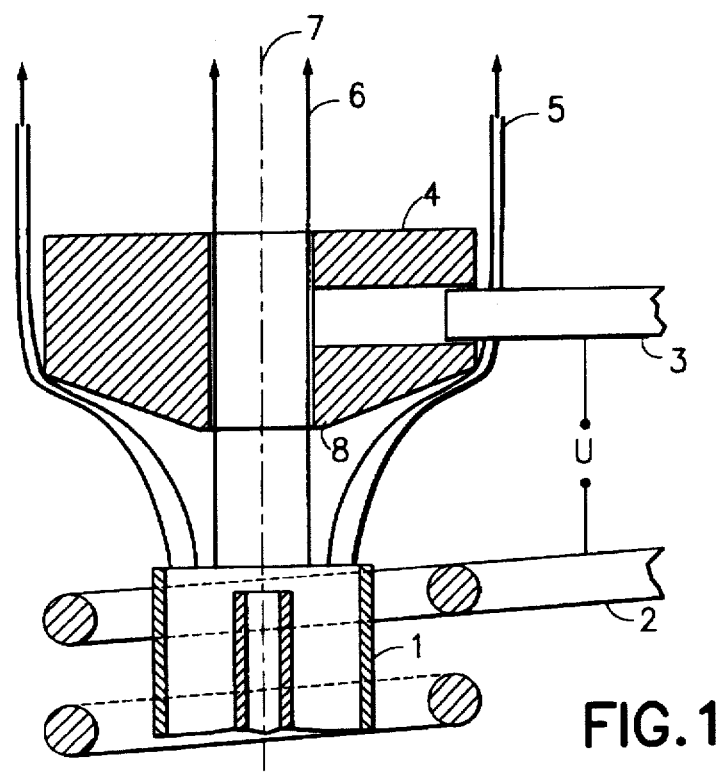

FIG. 1 illustrates a first exemplary embodiment of a simple variant of the device subject to the invention. FIG. 1 is explained below.

The ICP burner tube 1 with the concentric inner aerosol supply tube is surrounded by the high frequency excitation coil 2. Approximately 5 to 10 mm above the excitation coil is the axially located plasma manipulator 4 with the observation tube socket 3. Connectors for a water cooling device on the manipulator 4 have for reasons of clarity been omitted. The electric potential of the plasma manipulator 4 relative to the excitation coil is empirically optimized with the voltage source U.

The plasma located above the burner tube 1 is divided by the conically-shaped plasma manipulator 4 into a central jet 6 along the plasma axis 7 and a deflected jet 5. Depending on the opening of the plasma manipulator's 4 diaphragm, the central jet 6 has an approximate diameter of between 2 and 6 mm.

The emission radiation of the central jet 6 arrives at an optical spectrometer, which for reasons of clarity has been omitted, via an observation tube socket 3. It is advantageous to purge the observation tube socket 3 from the direction of the spectrometer with the plasma carrier gas when making measurements in the ultra violet spectral range.

The central bore hole of the plasma manipulator is selected such that depending on the dimensions of the ICP burner the central part of the plasma containing the atoms to be detected is allowed to pass and the outer ring-shaped region of higher temperature and higher baseline emission is masked off from the observation region. In this manner, the SNR (Signal/Noise Ratio) in such a device is increased when compared to the common free plasma torch.

Figure 2:
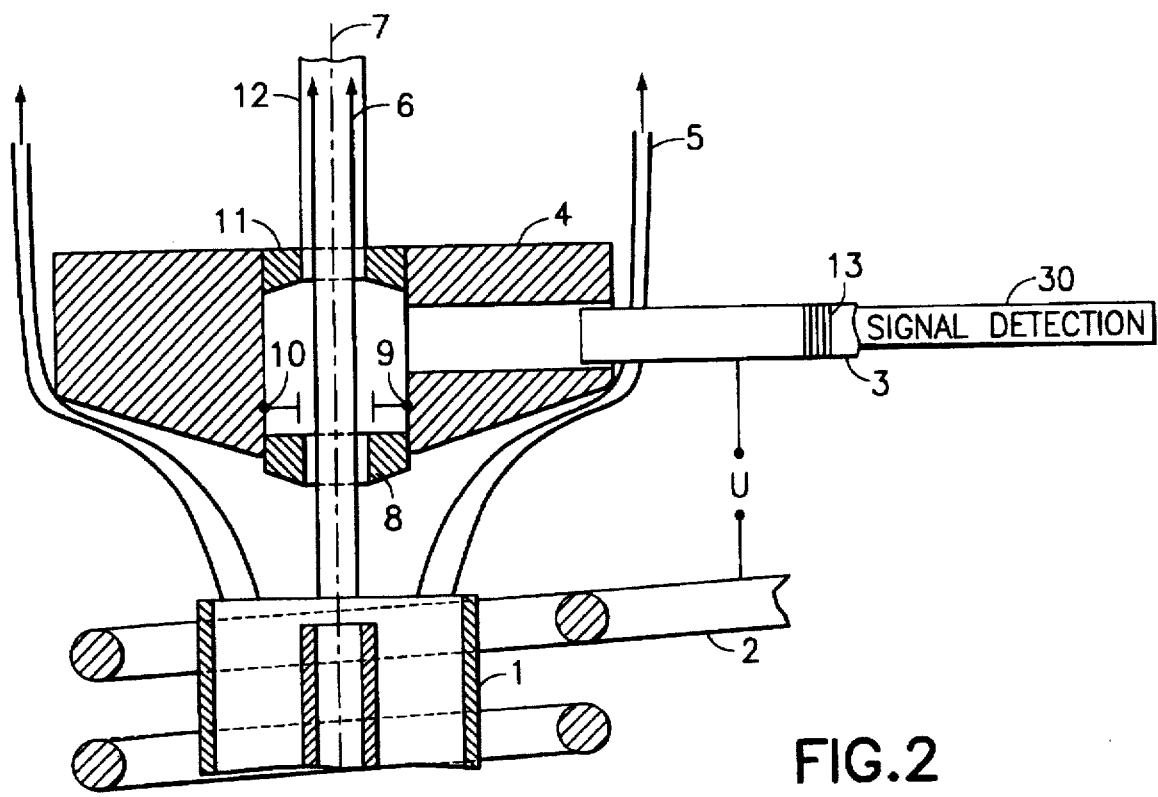
FIG. 2 is a second exemplary embodiment of the present invention.

FIG. 2 illustrates a second variant of the plasma manipulator. Here, the observation volume in the plasma manipulator 4 is expanded after the inlet diaphragm 8 which enables the installation of deflector electrodes 9 and 10. Latter may be installed immediately prior to the observation volume, as shown in FIG. 2, or on the side of the observation volume. A voltage applied to electrodes 9 and 10 removes charge carriers from the plasma jet, which reduces the baseline emission; the atomic emission on the other hand remains initially unchanged. The outlet diaphragm 11 prevents infiltration of atmospheric particles into the observation region. A tube socket 12 for connecting a pump may be incorporated in this diaphragm. In such a case, it is advantageous to provide an optical window 13 as a gas-tight seal between the observation tube socket 3 and the spectrometer.

Connecting a pump to tube socket 3 creates a reduced pressure in the plasma manipulator resulting in a heightened throughput of the central plasma jet and thus an increase in the emission signal.

The same criteria as mentioned for FIG. 1 apply to the selection of the input diaphragm's 8 diameter. Expanding the observation volume according to the embodiment illustrated in FIG. 2 results in reduced cooling of the central plasma jet 6 and therefore in a more uniform emission.

In place of or in addition to electrodes 9, 10, a means for generating a magnetic field, in particular a coil, may be installed at this point or subsequent to it in the direction of the flow. Preferably, the coil is arranged on a magnet core (yoke) with the coil being situated outside the plasma manipulator.

In an embodiment of the device not shown, but applicable to all three examples of the embodiment, the discharge end of the pump is led back to the analysis plasma, particularly into the cooling gas flow.

Figure 3:
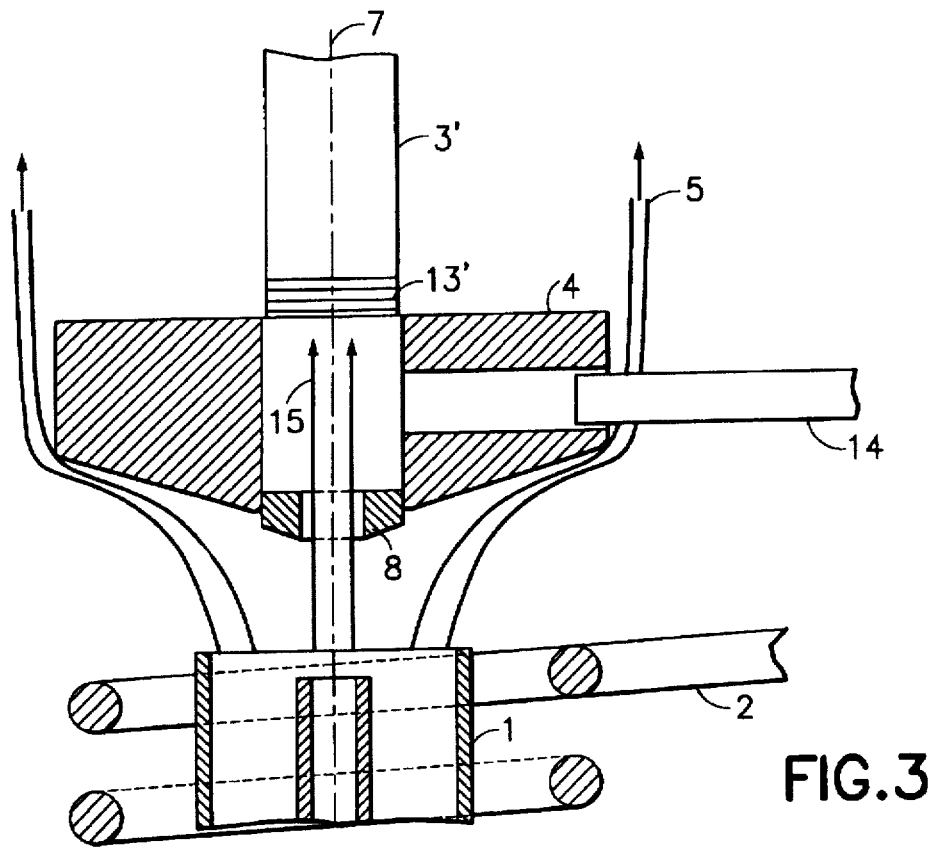
FIG. 3 is a third exemplary embodiment of the present invention.

Another variant of the invention is illustrated in FIG. 3. Here, the axis of the observation tube socket 3' coincides with the axis 7 of the analysis plasma. An optical window 13' providing a gas-tight seal for the observation device 3' is placed between the plasma manipulator 4 and the observation device 3' (observation tube socket). An image forming objective such as a concave mirror 19 having an axis running within the observation tube socket may be used in place of the window 13' to optimize light transmission from the cooled diaphragm to the spectrometer. A purging gas inlet 14 is situated on the side of the plasma manipulator 4 causing the purging gas as it exits the diaphragm 8 to prevent infiltration of the central part of the analysis plasma. The central beam 15 of the optical emission of the plasma passes into the observation device.

In this manner, only the optical emission of the central part of the analysis plasma, in particular also the ultra violet region, passes into the plasma manipulator 4.

The variant according to FIG. 3 is an easy to realize device which is also ideally suited for matrix-containing samples since no plasma particles reach the diaphragm 8 or the plasma manipulator 4. Leading back a portion of the plasma gas, as mentioned above, is advantageous for this embodiment as well. Using a pump, the gas is evacuated via a groove concentric with the diaphragm 8 and a separate bore hole in the plasma manipulator 4 and directed to the plasma burner 1. For reasons of clarity, this part of the device has been omitted in FIG. 3.

Figure 4:
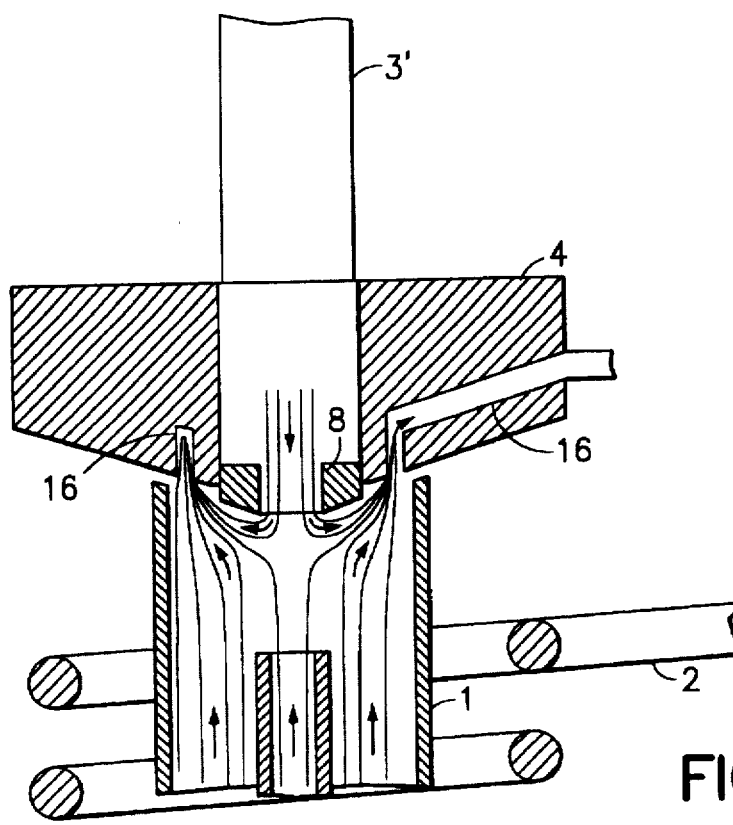
FIG. 4 is an exemplary embodiment of the present invention with an almost completely shielded plasma torch.
Figure 5:
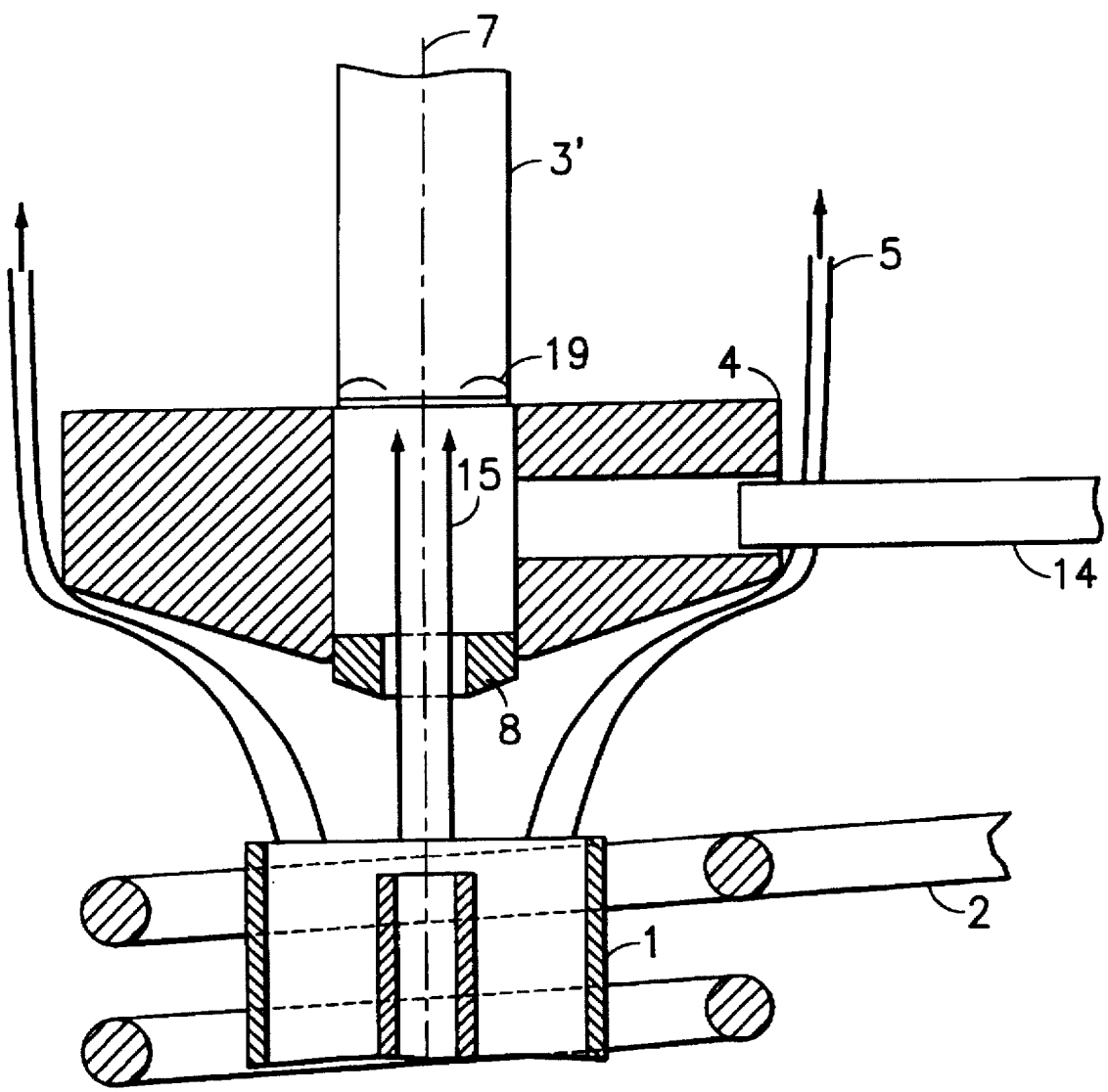
FIG. 5 illustrates an embodiment including an image-forming objective.

FIG. 4 illustrates another embodiment of the plasma manipulator according to the invention. In this embodiment, the ICP burner tube 1 is situated especially close to the plasma manipulator 4, and may, for instance, even be connected to the plasma manipulator 4. An inert gas, Argon for instance, flows through the tube socket 3 in opposite direction of the plasma torch flow, which in the embodiment shown in FIG. 4 flows from bottom to top. The inert gas flow exits via the opening of diaphragm 8 and there meets the carrier gas flow of the plasma torch concentrically. The plasma torch is dissipated in a funnel-like shape in the region where the gas flows meet and enters an annular gap shaped evacuation device 16. The inert gas, the carrier gas of the plasma torch and aerosol remnants are all evacuated through the annular gap. The cooled down gas may be cleaned and reused as carrier gas. Since the ICP burner tube 1 essentially surrounds the diaphragm 8 and the annular gap 16, contact between the plasma flame and the ambient atmosphere is practically avoided, thus eliminating disturbing interferences.

It is advantageous to dissipate the thermal energy of the plasma torch through water cooling of the plasma manipulator 4.

This configuration allows particularly good observation conditions of the portion of the plasma torch to be viewed. The spectrometer input may, for instance, be situated in the axis of the plasma torch, i.e., concentrically inside tube socket 3'. This allows for a so-called end-on observation position of the central portion of the ICP plasma. Particularly good selectivity of the individual elements to be observed can be achieved by adjusting the length of the plasma torch, or more specifically, the central portion of the plasma torch, by means of the flow of a gas supplied in counter direction. Then, only the portion of the plasma torch containing the interesting emissions will be viewed. To measure Cadmium, for instance, the length of the plasma torch would be short so that only the hotter portions would be analyzed, while a longer plasma torch would be used to analyze Sodium, so that only the cooler regions containing the sodium emission characteristics will be available for observation.

I claim:

1. Device for emission spectrum analysis with an analysis plasma containing the analysis sample, wherein there is a plasma manipulator (4) with a cooled diaphragm (8) concentric with the axis (7) of and perpendicular to the direction of expansion of the plasma with a free diameter smaller than that of the plasma which allows only an optically active part (6) of the analysis plasma to pass through said diaphragm and masks off a remaining region, and an observation device (3, 3') adapted for observing the radiation emitted by the volume of plasma allowed through.

2. Device according to claim 1, wherein the observation device (3, 3') is situated at an observation angle between 10 and 170 degrees with respect to an expansion axis (7) of the plasma.

3. Device according to claim 1, wherein the axis of the observation device (3'), and of an observation tube socket thereof, coincides with the axis (7) of the analysis plasma allowed through centrally, or its optical portion respectively.

4. Device for emission spectrum analysis according to claim 1, wherein said cooled diaphragm (8) has a thickness about equal to its diameter and an observation volume has a diameter greater than that of the diaphragm.

5. Device for emission spectrum analysis according to claim 1, wherein electrodes (9,10) as a means to generate an electrical field, are situated between the cooled diaphragm (8) and the observation volume, specifically in the region of the observation volume in a spatial area adjacent to the masked-off part of the analysis plasma (6).

6. Device for emission spectrum analysis according to claim 1, further comprising a pair of electrodes (9, 10) located on opposing sides of said plasma (6) allowed through said cooled diaphragm (8), and signal detection means (30) in said observation device (3), and wherein an alternating voltage is applied to the electrodes (9, 10) with signal detection in said observation device being synchronized with the phase of the alternating voltage.

7. Device for emission spectrum analysis according to claim 1, wherein the plasma manipulator (4) contains, at an outlet of said optically active part of the analysis plasma (6), a second diaphragm (11) connected to a tube socket (12) for connecting a pump and wherein an observation tube socket forming part of said observation device (3) has an optical window (13) serving as a gas-tight seal.

8. Device for emission spectrum analysis according to claim 7, wherein the discharge side of the pump is led back to the analysis plasma.

9. Device for emission spectrum analysis according to claim 1, wherein the plasma manipulator (4) is a hollow body made of metal with cooling water flowing through it and further comprising pressed-in or screwed-on diaphragms (8, 11) made of graphite.

10. Device for emission spectrum analysis according to claim 3, wherein the observation tube socket (3), is equipped with a connection for a purging gas, and with an optical window (13) serving as a gas-tight seal.

11. Device for emission spectrum analysis according to claim 3, wherein the plasma manipulator (4) is formed with a bore-hole inside in the line with the observation tube socket (3) and said bore hole contains a concave mirror with its axis running within the observation tube socket (3).

12. Device for emission spectrum analysis according to claim 1, further comprising a gas-tight optical Window (13') between said cooled diaphragm (8) and said observation device (3') and a purge gas inlet (14) at the plasma manipulator (4) which so directs purging gas through said cooled diaphragm that the purging gas exits the cooled diaphragm (8) in the direction of a source of the analysis plasma.

* * * * *

UNITED STATES PATENT AND TRADEMARK OFFICE
CERTIFICATE OF CORRECTION

PATENT NO. : 5,731,872
DATED : Mar. 24, 1998
INVENTOR(S) : Falk

It is certified that error appears in the above-identified patent and that said Letters Patent is hereby corrected as shown below:

In column 5, line 6, "gas-fight" should be --gas-tight--.

Signed and Sealed this

Twenty-seventh Day of April, 1999

Attest:

Attesting Officer

Q. TODD DICKINSON

Acting Commissioner of Patents and Trademarks